(12) United States Patent
Headrick

(10) Patent No.: US 7,549,319 B2
(45) Date of Patent: Jun. 23, 2009

(54) HIGH PRESSURE RESONANT VIBRATING-TUBE DENSITOMETER

(75) Inventor: Dick C. Headrick, Duncan, OK (US)

(73) Assignee: Halliburton Energy Services, Inc., Duncan, OK (US)

( * ) Notice: Subject to any disclaimer, the term of this patent is extended or adjusted under 35 U.S.C. 154(b) by 173 days.

(21) Appl. No.: 11/560,772

(22) Filed: Nov. 16, 2006

(65) Prior Publication Data

US 2008/0115577 A1    May 22, 2008

(51) Int. Cl.
    *G01N 9/02*      (2006.01)
    *G01F 1/84*      (2006.01)

(52) U.S. Cl. .................. 73/32 A; 73/861.357
(58) Field of Classification Search ........... 73/32 A, 73/861.355, 861.357
See application file for complete search history.

(56) References Cited

U.S. PATENT DOCUMENTS

| | | | |
|---|---|---|---|
| 3,444,723 A | 5/1969 | Wakefield | 73/32 A |
| 3,955,401 A * | 5/1976 | Catherall | 73/32 A |
| 4,491,009 A | 1/1985 | Ruesch | 73/32 A |
| 4,622,858 A | 11/1986 | Mizerak | 73/861.357 |
| 4,680,974 A | 7/1987 | Simonsen et al. | 73/861.357 |
| 4,768,384 A | 9/1988 | Flecken et al. | 73/861.02 |
| 4,803,867 A * | 2/1989 | Dahlin | 73/32 A |
| 5,226,330 A * | 7/1993 | Lew | 73/861.357 |
| 5,497,665 A | 3/1996 | Cage et al. | 73/861.356 |
| 5,576,500 A | 11/1996 | Cage et al. | 73/861.357 |
| 5,602,345 A | 2/1997 | Wenger et al. | 73/861.357 |
| 5,850,039 A * | 12/1998 | Van Cleve et al. | 73/861.357 |
| 6,264,244 B1 | 7/2001 | Isennock et al. | 285/55 |
| 6,327,915 B1 | 12/2001 | Van Cleve et al. | 73/861.357 |
| 6,374,478 B1 * | 4/2002 | Neece et al. | 29/595 |
| 6,378,364 B1 * | 4/2002 | Pelletier et al. | 73/152.47 |
| 6,460,796 B1 | 10/2002 | Berning et al. | 242/407 |

(Continued)

FOREIGN PATENT DOCUMENTS

JP      09113433 A * 5/1997

(Continued)

OTHER PUBLICATIONS

XP002939192 "Mass Flowmeters" 1991, Proceedings of the Instrument Society of America Conference.

(Continued)

*Primary Examiner*—Hezron Williams
*Assistant Examiner*—Tamiko D Bellamy
(74) *Attorney, Agent, or Firm*—John W. Wustenberg; Conley Rose, P.C.

(57) ABSTRACT

A method of manufacturing a high pressure vibrating tube densitometer comprising enclosing twin flow tubes within an outer shell, wherein the outer shell comprises portals for the installation or replacement of internal components. A vibrating tube densitometer system for determining the density of a high pressure fluid in a pipeline, the system comprising a densitometer in communication with a controller, the densitometer comprising twin straight flow tubes spaced parallel apart within an outer shell comprising one or more portals for the placement of internal components, wherein the controller is in signal communication with a signal pickup, a tube driver, and the at least one temperature or pressure sensor and calculating the density of a fluid having a pressure of greater than 1500 psi.

13 Claims, 3 Drawing Sheets

U.S. PATENT DOCUMENTS

| | | |
|---|---|---|
| 6,732,570 B2 | 5/2004 | Francisco, Jr. .............. 73/32 A |
| 6,868,740 B2 | 3/2005 | Hussain ................. 73/861.356 |
| 2004/0123645 A1 | 7/2004 | Storm et al. ................ 73/32 A |
| 2006/0144136 A1 | 7/2006 | Dutton et al. ............ 73/152.32 |

FOREIGN PATENT DOCUMENTS

| | | |
|---|---|---|
| WO | WO 9608967 A1 | 3/1996 |
| WO | WO 01/51898 | 7/2001 |

OTHER PUBLICATIONS

Foreign communication related to a counterpart application dated Feb. 28, 2008.

\* cited by examiner

HIGH PRESSURE RESONANT VIBRATING-TUBE DENSITOMETER

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The present disclosure relates to an apparatus and method for making the apparatus used to determine the density of a high pressure fluid. More particularly, the present disclosure is directed to a high pressure vibrating-tube densitometer and a method for making a high pressure vibrating tube densitometer, the densitometer operable at fluid pressures greater than 1500 psi.

2. Background of the Invention

A natural resource such as oil or gas residing in a subterranean formation can be recovered by drilling a well into the formation. The subterranean formation is usually isolated from other formations using a technique known as well cementing. In particular, a wellbore is typically drilled down to the subterranean formation while circulating a drilling fluid through the wellbore. After the drilling is terminated, a string of pipe, e.g., casing, is run in the wellbore. Primary cementing is then usually performed whereby a cement slurry is pumped down through the string of pipe and into the annulus between the string of pipe and the walls of the wellbore to allow the cement slurry to set into an impermeable cement column and thereby seal the annulus. Subsequent secondary cementing operations, i.e., any cementing operation after the primary cementing operation, may also be performed. Examples of secondary cementing operations include squeeze cementing whereby a cement slurry is forced under pressure to areas of lost integrity in the annulus to seal off those areas, and the setting of temporary or permanent cement plugs in order to seal off a desired region of the wellbore.

The well extends through various zones in the earth that the drilling crew may wish to tap. To tap a certain zone, a portion of the casing in the desired zone is fractured. Once the casing is fractured, a fracture fluid is pumped into the fracture to keep it open. The fracture fluid holds the fracture open while still being permeable. Oil and gas is thus able to flow through the fracture and into the wellbore.

In many instances, it is desirable to know the density of the cement or the density of the fracturing fluid in such oil field operations. Conventionally, this is accomplished with the use of nuclear densitometers. However, although these radioactive sensors provide an accurate and compact means of measuring fluid density, there are many problems associated with the use of these nuclear densitometers, and in this time of increasing security, these problems have been escalating recently.

One problem associated with nuclear densitometers is that interstate and international transport of nuclear densitometers can be a difficult process due to the numerous and severe laws and regulations regarding nuclear technology. Another concern is the safe handling and transport of nuclear densitometers. Further, the operators of nuclear densitometers have to be certified or licensed by the proper regulating agency. These health and safety issues, shipping difficulties, and record-keeping burdens motivate development of non-radioactive alternatives for fluid density determination.

Accordingly, an ongoing need exists for a non-radioactive apparatus, and a method for making this apparatus, for determining the density of a fluid at high pressures, such as those encountered in the oil field. In particular, there is a need for such a non-radioactive apparatus and a method for making same, wherein the apparatus can be operated at pressures above 1500 psi. This apparatus, in addition to a high working pressure rating, will preferably also have a high pressure proof rating, provide strong resonance, exhibit limited sensitivity to the stiffness and the loading of the adjacent manifolding, and be compact, lightweight, and erosion-resistant.

BRIEF SUMMARY OF SOME OF THE PREFERRED EMBODIMENTS

Disclosed herein is a method of manufacturing a high pressure vibrating tube densitometer comprising enclosing twin flow tubes within an outer shell, wherein the outer shell comprises portals for the installation or replacement of internal components.

Further disclosed herein is a vibrating tube densitometer system for determining the density of a high pressure fluid in a pipeline, the system comprising a densitometer in communication with a controller, the densitometer comprising twin straight flow tubes spaced parallel apart within an outer shell comprising one or more portals for the placement of internal components, said internal components further comprising a driver positioned adjacent the twin flow tubes for initiating and maintaining resonant vibration of the twin flow tubes; at least one pickup positioned adjacent the twin flow tubes for sensing the motion of at least one twin flow tube and transmitting a signal indicative of the response of the vibration of the at least one flow tube; and at least one temperature or pressure sensor, wherein the controller is in signal communication with the pickup, the driver, and the at least one temperature or pressure sensor and calculating the density of a fluid having a pressure of greater than 1500 psi. The portals may be reversibly sealable. The outer shell may comprise hammer unions and wherein the densitometer has been ruggedized to withstand the force applied to the hammer unions when connecting the densitometer to the pipeline. The densitometer may comprise at least one temperature sensor and at least one pressure sensor. The densitometer may comprise two temperature sensors, for example at least one temperature sensor positioned to determine the temperature of the twin flow tubes and at least one temperature sensor positioned to determine the temperature of the outer shell. The controller may be capable of calculating fluid density compensated for temperature and pressure.

Further disclosed herein is a method of determining the density of a wellbore servicing fluid comprising pumping the fluid at a pressure of greater than or equal to 1500 psi to a resonant vibrating tube densitometer comprising twin vibrating flow tubes wherein resonant vibrations of at least one of the fluid-filled vibrating tubes are used to determine the density of the high pressure fluid.

Further disclosed herein is a method of manufacturing a high pressure vibrating tube densitometer comprising providing twin flow tubes, wherein the twin flow tubes are straight tubes made of the same resilient material having uniform bores, and each twin flow tube has an inlet end and an outlet end; optionally providing one or two end sections connected to the inlet end, outlet end, or both of the twin flow tubes; and enclosing the twin flow tubes and the optional end sections within an outer shell, wherein the outer shell comprises one or more portals for the installation and replacement of internal components. The twin flow tubes, the optional one or two end sections, and the outer shell may be heat treated to develop hardness. A sensor support structure may be formed by welding together the main components such that the outer shell maintains an even space between adjacent parallel flow tubes along their length and prevents axial loading on the twin flow tubes. The end sections connect to inlets and/or outlets on the twin flow tubes. An inlet end section may be formed by attaching flow tube inlets to dual stream dividing tubes such that, during operation of the densitometer, the fluid flow into the inlet flow tube is essentially evenly divided between the dual stream dividing tubes. An outlet end section may be formed by attaching flow tube outlets to dual stream combining tubes such that, during operation of the densitometer, the fluid flow from the flow tubes is combined into a single outlet flow tube. For example, the free end of each inlet stream dividing tube of the inlet end section may be attached to the inlet end of one of the twin flow tubes. Likewise, the free end of each outlet stream dividing tube of the outlet end section may be attached to the outlet end of one of the twin flow tubes. In an embodiment, an end section is U-shaped end section attached to the outlet end of one twin flow tube and the inlet end of the other twin flow tube. The heat treatment of one or more components of the densitometer, for example the end sections, may yield a Brinell hardness of from 270 to 301. Various components of the densitometer such as the flow tubes, outer shell, end sections may be welded together, and such components may be heat treated before welding, after welding, or both. In an embodiment, the welded assembly of components is heat treated to relieve stress on the welds. In an embodiment, the stress relief heat treatment comprises heating the sensor support structure at a temperature of between 900° F. and 1000° F. for 4 hours. The end sections may comprise alloy steel with a hardness of from 270 to 301 HB, the twin flow tubes may comprise alloy steel with a hardness of from 270 to 301 HB, and the outer shell may comprise carbon steel having a hardness between 100 HB and 400 HB. Internal components may be installed within the sensor support structure by way of the one or more portals. The internal components may comprise at least a driving means for exciting vibrations of the central portions of the twin flow tubes and at least one pickup to detect the response of vibration of at least one of the twin flow tubes and provide a signal representative of the frequency of the vibrations. The at least one pickup may comprise a piezo-based accelerometer or a magnet-coil velocity sensor. At least one temperature or pressure sensor may be installed within the sensor support structure. At least one temperature sensor may be positioned on at least one of the twin flow tubes, on the support structure, or on a combination thereof. The temperature sensor may be selected from the group consisting of thermocouples, resistive temperature devices, thermistors, and combinations thereof. The temperature or pressure sensor may comprise a transducer, which may be mounted downstream of the densitometer. The driving means may comprise a driver magnet attached to one twin flow tube and a coil attached opposite the driver magnet on the other twin flow tube. The driving means may be located midway along the length of the twin flow tubes. The pickup may be located adjacent the driving means. Upon installation of the internal components the portals may be closed and sealed in such a way as to allow high pressure operation of the densitometer and reopened to allow removal and replacement of internal components. The densitometer is suitable for use at high pressures, for example equal to or greater than 1500, 5000, or 10000 psi. The outer shell may have a cross-sectional area about 4 to 6 times the cross-sectional area of the twin flow tubes.

The foregoing has outlined rather broadly the features and technical advantages of the present disclosure in order that the detailed description that follows may be better understood. Additional features and advantages of the apparatus and method will be described hereinafter that form the subject of the claims of this disclosure. It should be appreciated by those skilled in the art that the conception and the specific embodiments disclosed may be readily utilized as a basis for modifying or designing other structures for carrying out the same purposes of the present disclosure. It should also be realized by those skilled in the art that such equivalent constructions do not depart from the spirit and scope of the apparatus and method as set forth in the appended claims.

BRIEF DESCRIPTION OF THE DRAWINGS

For a detailed description of the preferred embodiments of the apparatus and method for making the apparatus of the present disclosure, reference will now be made to the accompanying drawings in which.

DETAILED DESCRIPTION OF THE PREFERRED EMBODIMENTS

Disclosed herein are various embodiments of a high pressure vibrating tube densitometer, hereinafter HPVT densitometer. The HPVT densitometer comprises parallel straight vibrating flow tubes as well as a driving means for initiating vibration of the fluid-filled flow tubes and a pickup means for sensing these vibrations from which fluid density is determined. The term "vibrating" flow tubes is used herein for ease of reference, however, it should be understood that, oftentimes, the tubes are only actually "vibrating" during use of the densitometer.

Also disclosed herein are methods for the manufacture of the HPVT densitometer. In some embodiments, these methods of manufacture comprise a welded construction and the formation of a pre-sensor assembly (hereinafter PSA) comprising the main non-temperature-sensitive components of the HPVT densitometer and portals for the post-heat treatment placement of temperature-sensitive internal components such as the driving means, the pickup means, and sensors as will be further discussed hereinbelow. As used herein, the term "non-temperature-sensitive" refers to components that are oven-tolerant, i.e. heat-tolerant.

The HPVT densitometer may be used for determining, in a non-radioactive manner, the density of high pressure fluids, for example, various oil field fluids, as described further herein. In embodiments, the HPVT densitometer may be used to determine the density of a fluid at a pressure above 1500 psi with a desirable accuracy. In an embodiment, the HPVT densitometer is a non-radioactive apparatus that has a nominal flow path of from 2 inches to 4 inches, a working pressure of from equal to or greater than 1500 psi and less than or equal to 15,000 psi, and an accuracy of ±0.2 pounds per gallon, ppg. In an embodiment, the apparatus is rated for a working pressure of from equal to or greater than 1500 psi up to 2,000 psi, alternatively up to 5,000 psi, alternatively up to 10,000 psi, alternatively up to 15,000 psi. In an embodiment, the proof pressure capability of the HPVT densitometer is equal to or greater than 1500 psi up to 20,000 psi, alternatively up to 22,500 psi.

Figure 1:
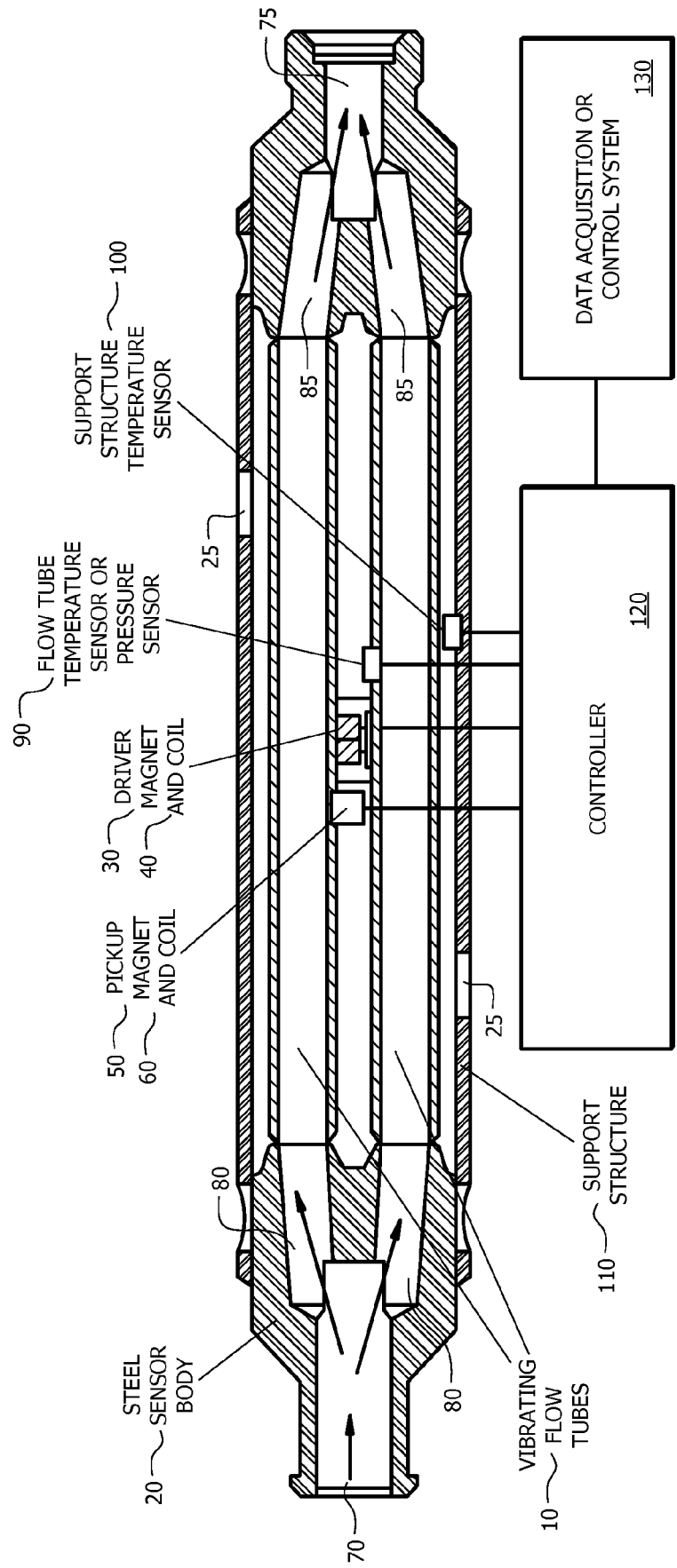
FIG. 1 is a depiction of a first embodiment of an apparatus of the present disclosure.

In embodiments, the HPVT densitometer has any sensor body configuration that provides flow through parallel straight tubes. For example, FIG. 1 shows a HPVT densitometer according to an embodiment of this disclosure. The PSA of the embodiment shown in FIG. 1 comprises two crude Y-shaped end sections, inlet end section 70/80 and outlet end section 75/85, twin vibrating flow tubes 10, and an outer shell comprising steel sensor body 20 and support structure 110. Support structure 110 serves to prevent axial loading on the twin vibrating flow tubes 10. In embodiments, the twin straight vibrating flow tubes 10 are spaced apart in a rigid body, for example steel sensor body 20 having support structure 110 such that the vibrating flow tubes 10 may vibrate transversely in anti-phase.

The embodiment of FIG. 1 incorporates a crude Y-shaped inlet end section, comprising inlet tube 70 and inlet stream dividing tubes 80, and a similar outlet end section, comprising outlet stream dividing tubes 85 and outlet tube 75. Fluid enters the HPVT densitometer through inlet tube 70 and is split into two parallel and comparable streams through inlet stream-dividing tubes 80 that are attached to the inlet end of the twin vibrating flow tubes 10. Fluid exits the HPVT densitometer through corresponding outlet stream dividing tubes 85 that are attached to the outlet ends of the twin vibrating flow tubes and combined at outlet tube 75.

The outer shell of the PSA comprises one or more portals 25 for the post-heat treatment placement of temperature-sensitive internal components, as will be disclosed hereinbelow. The temperature-sensitive internal components of the HPVT densitometer of FIG. 1 comprise a driver assembly for initiating and maintaining vibration of the twin vibrating tubes 10, a pickup assembly for detecting the motion of the twin vibrating flow tubes 10 and pass a corresponding electronic pickup response signal to controller 120, and at least one sensor for determining temperature and/or pressure at various parts of the system. In embodiments such as shown in FIG. 1, the driver assembly comprises an electromagnet comprising a permanent driver magnet 30 mounted on one of the twin vibrating flow tubes 10 that is acted upon by a driver coil 40 mounted on the second vibrating flow tube to supply a fluctuating force to excite vibration. The pickup assembly of the embodiment of FIG. 1 is a magnet-coil velocity sensor comprising a pickup magnet 50 and pickup coil 60. Alternatively, the pickup may be a piezo-based accelerometer. The driver assembly and the pickup assembly are disposed in the void between the twin vibrating flow tubes 10.

As discussed in more detail hereinbelow, it may be desirable to correct the density as measured by the HPVT densitometer for the effects of temperature. In these embodiments, the HPVT densitometer may comprise at least one sensor for the determination of the temperature at one or more locations within the densitometer. In the embodiment of FIG. 1, flow tube temperature sensor 90 is affixed to one of the flow tubes 10 and support structure temperature sensor 100 is attached to support structure 110.

Flow tube temperature sensor 90 and support structure temperature sensor 100 are any sensors capable of measuring the temperature of the vibrating flow tubes 10 and the support structure 110, respectively. In an embodiment, the flow tube temperature sensor is a thermocouple. In an embodiment, the flow tube temperature sensor is a resistive temperature device, RTD. In an embodiment the flow tube temperature sensor is a thermistor. In an embodiment, the support structure temperature sensor is a thermocouple. In an embodiment, the support structure temperature sensor is a resistive temperature device, RTD. In an embodiment the support structure temperature sensor is a thermistor. In an embodiment, multiple temperature sensors are used on the vibrating flow tubes to improve the accuracy of the flow tube temperature measurement. In an embodiment, multiple temperature sensors are used on the support structure to improve the accuracy of the support structure temperature measurement. In embodiments, temperature sensors are located on other parts of the HPVT densitometer to determine the temperature on parts other than or in addition to the flow tubes and/or the support structure.

It may also be desirable to correct the density as measured by the HPVT densitometer for the effects of pressure as discussed in more detail hereinbelow. In these embodiments, the HPVT densitometer may comprise at least one sensor for the determination of fluid pressure. Fluid pressure may be measured, for example, by a transducer mounted downstream of the densitometer.

Meter electronics, or any other ancillary electronics or circuitry connected to the densitometer, receive the pickup and sensor signals and send signals to the driver. In FIG. 1, controller 120 is in communication with the pickup assembly, the driver assembly, and the temperature sensors, 90 and 100. Data acquisition or control system 130 obtains or supplies information to or from the controller 120. Controller 120 may be a collection of commercially available electronic components. Controller 120 may comprise a control module that generates the twin vibrating flow tube excitation signals and reads the pickup and any additional sensor signals. The controller 120 may also comprise a microprocessor that reads fluid pressure, calculates density and outputs the density value to, for example, a data acquisition system 130. The controller 120 may also contain power supplies for various components, such as the accelerometer, the control module, the microprocessor, or combinations thereof.

In various embodiments, the HPVT densitometer comprises at least one amplifier to amplify one or more signals. For example, an amplifier may be used to boost the signal from the controller 120 to the driver coil 40. In embodiments, the control module may contain an amplifier to boost the pickup signal. In embodiments, the at least one amplifier is an audio amplifier.

In embodiments, the outer shell of the HPVT densitometer of the present disclosure comprises hammer unions on each end to facilitate the connection of the HPVT densitometer to a connected pipeline, as discussed hereinbelow. In embodiments, the end connections of the HPVT densitometer are standard size hammer unions, for example, "FIG. 1502" hammer unions.

A second embodiment according to the present disclosure, the use of which is discussed further hereinbelow, is the U-tube sensor configuration shown in FIG. 2. In this embodiment, the PSA comprises twin straight vibrating flow tubes 10 connected at one end with U-shaped end section 140 and spaced parallel apart, as in the embodiment of FIG. 1, within an outer shell comprising steel sensor body 20 and support structure 110. Again, the PSA comprises portals 25 for the post heat treatment placement of temperature-sensitive internal components, as in the embodiment of FIG. 1. The driver assembly, comprising driver magnet 30 and driver coil 40 are oppositely positioned at approximately the midpoint of the vibrating flow tubes 10, as in the embodiment of FIG. 1. For clarity, vibration pickup(s) assembly(ies), temperature sensors, pressure sensors, controller, and the data acquisition and control system are not shown, but may be present in the embodiment of FIG. 2, as for the embodiment of FIG. 1.

Figure 2:
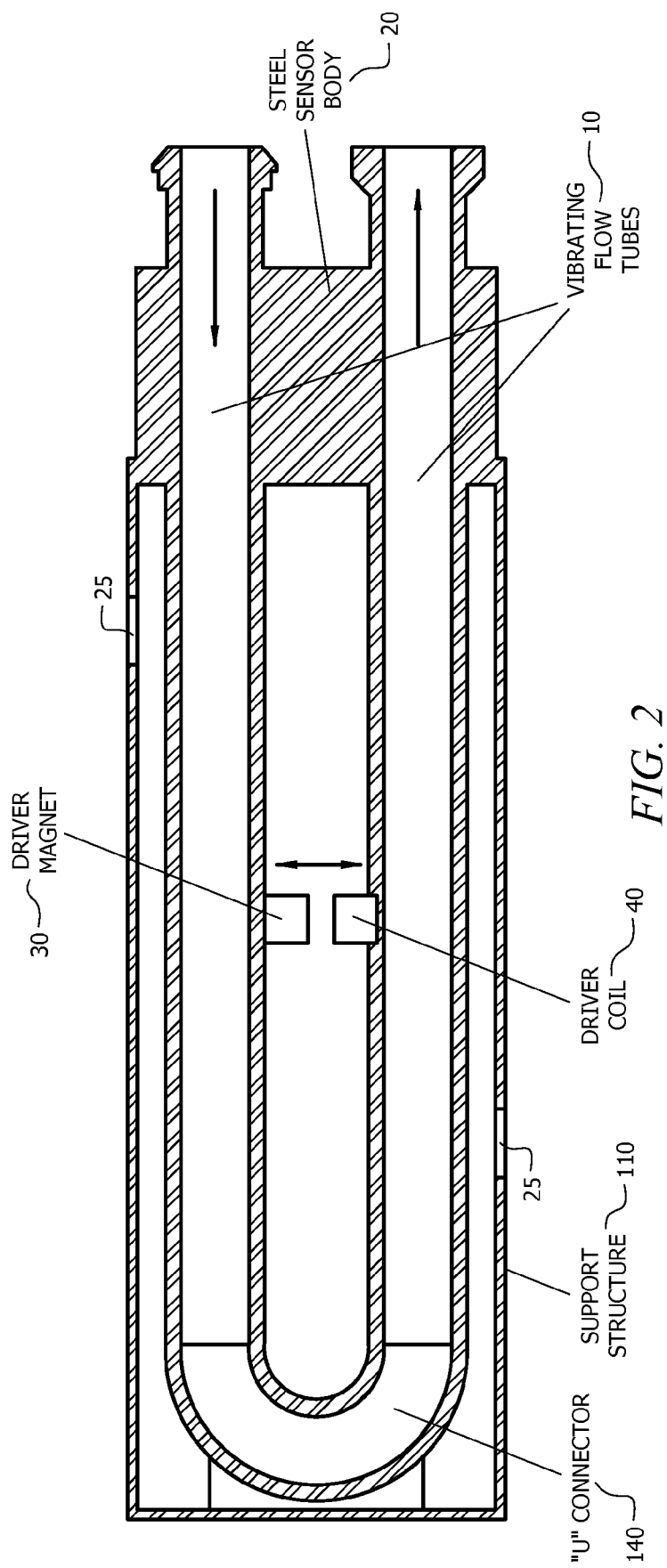
FIG. 2 is a depiction of a second embodiment of an apparatus of the present disclosure.
Figure 3:
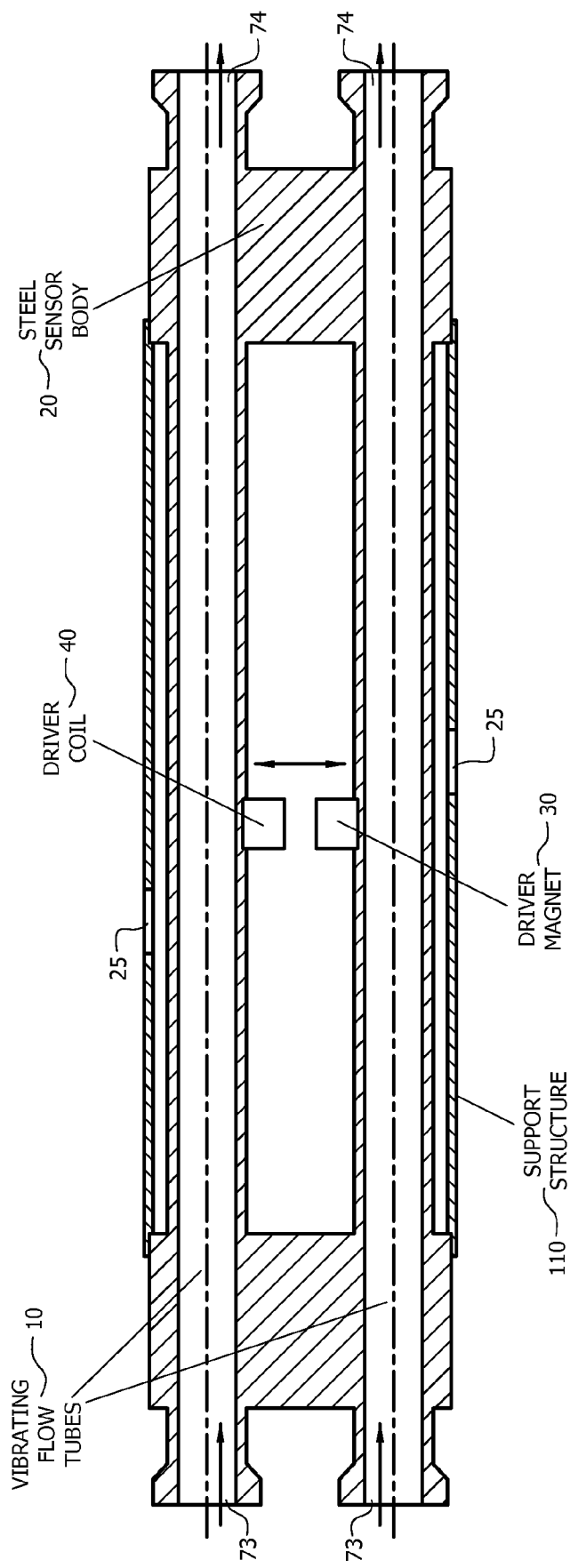
FIG. 3 is a depiction of a third embodiment of an apparatus of the present disclosure.

A third embodiment according to the present disclosure is a sensor body configured with dual inlets 73 and outlets 74 as shown in FIG. 3. In this embodiment, the PSA comprises twin straight vibrating flow tubes 10 spaced apart within an outer shell comprising steel sensor body 20 and support structure 110, as in the embodiments of FIGS. 1 and 2, and the PSA comprises portals for the post-heat treatment placement of internal components. Again, the driver assembly, comprising a driver magnet 30 and driver coil 40 are oppositely positioned on the vibrating flow tubes 10 approximately midway along the length of the vibrating flow tubes 10. For this simple configuration, the splitting and recombining of the flow is performed by the connected pipeline as discussed hereinbelow. As with FIG. 2, vibration pickup(s) assembly(ies), temperature sensors, pressure sensors, controller, and the data acquisition and control system are not shown, but may be present in the embodiment of FIG. 3, as for the embodiment of FIG. 1.

The method of manufacture of the apparatus of the present disclosure as described herein is complicated by the material requirements that enable use of the apparatus for measuring the density of high pressure fluids.

In order to manufacture a densitometer capable of operating at pressures higher than 1500 psi, the HPVT densitometer of the present disclosure is made of strong materials, has thick walls on its vibrating flow tubes, and has a simplified design (no bends, for example). The wall thickness of the vibrating flow tubes of the HPVT densitometers of the present disclosure is three to four times that of the wall thickness of the vibrating flow tubes in low pressure vibrating tube densitometers. The HPVT densitometer of the present disclosure also contains no flexible seal elements, as these flexible, e.g. rubber, seal elements would not be viable at the high pressures for which the HPVT densitometer is manufactured.

The use of stronger materials mandates a complicated manufacturing process that is further discussed hereinbelow. The manufacture of the HPVT densitometers of the present disclosure involves heat treatment of the main non-temperature-sensitive components of the PSA pre-welding, as well as heat treatment of the assembled PSA post-welding. As mentioned above, the PSA includes portals for the post-heat treatment installation of the temperature-sensitive internal components, as discussed hereinbelow.

In an embodiment, the vibrating flow tubes are constructed of high strength steel. In an embodiment, the vibrating flow tubes are constructed from alloy steel commonly known as 4130. For compatibility with operating fluids and pressures, materials used for the pressure containing components are heat treated, as described hereinbelow, to 270-301 HB. In an embodiment, the vibrating flow tubes have a wall thickness of 0.28 inches. In an embodiment, the vibrating flow tubes have an inside diameter of 1.34 inches and an outside diameter of 1.9 inches. In an embodiment, the vibrating flow tubes have a wall thickness of 0.38 inches. In an embodiment, the vibrating flow tubes have an inside diameter of 1.87 inches and an outside diameter of 2.62 inches.

In an embodiment, the end sections comprise high strength alloy steel. For example, in the embodiment of FIG. 1, the inlet end section and the outlet end section comprising inlet tube 70 and inlet stream dividing tubes 80 and outlet tube 75 and outlet stream dividing tubes 85 respectively, may be constructed of high strength alloy steel. A steel suitable for this purpose is 4324 alloy steel. As discussed hereinbelow, the 4324 components are heat treated to 270-301 HB. In an embodiment, inlet tube 70 and outlet tube 75 have an inside diameter of 1.87 inches (nominal 2 inches). In an embodiment, inlet tube 70 and outlet tube 75 have an inside diameter of 3 inches. In an embodiment, inlet stream dividing tubes 80 and outlet stream dividing tubes 85 have a nominal diameter of 2 inches, actual diameter 1.87 inches. In an embodiment, inlet stream dividing tubes 80 and outlet stream dividing tubes 85 have an inside diameter of 1.31 inches.

The outer shell is not subjected to the high pressure flow, as are the end sections and the twin vibrating flow tubes, and, as such, the outer shell may comprise a lower strength alloy steel that provides the stiffness necessary to carry axial loads and hold the end sections rigidly in place. A suitable steel is SA53, 1018, or 1026 alloy. A suitable steel has a hardness of from about 100 HB to about 400 HB. In an embodiment, the outer shell has a cross sectional area about 4 to 15 times that of the vibrating flow tubes. In embodiments the shell-to-flow-tube area ratio is about 10-15. In embodiments, the shell-to-flow-tube ratio is about 4 to 6. In embodiments, the outer shell has an outside diameter of 8.625 inches and an inside diameter of 7.625 inches. In embodiments, the outer shell has an outside diameter of 6.625 inches and an inside diameter of 5.761 inches. In embodiments, the outside diameter is greater than 8.625 inches.

In an embodiment, the main non-temperature-sensitive components are heat treated as known in the art to develop necessary hardness. For example, the main non-temperature-sensitive components of the PSA of the HPVT densitometer of FIG. 1 are the two end sections comprising inlet tube 70 and inlet stream-dividing tubes 80 on the inlet side, and outlet tube 75 and outlet stream-dividing tubes 85 on the outlet side of the apparatus; the twin vibrating flow tubes, 10; and the outer shell, comprising the steel sensor body 20 and the support structure 110.

In embodiments, the heat treatment of the main non-temperature-sensitive components of the PSA is a quench and temper process as is known to those of skill in the art. In embodiments, the tempering of the main components of the PSA occurs in the temperature range of from 700° F. to 1300° F. for a duration of one hour minimum plus one additional hour for each inch of thickness or fraction thereof greater than one inch. In an embodiment, the end sections are made from 4324 alloy steel and are heat treated at the tempering temperature of 1050° F. for one hour minimum plus one additional hour for each inch of thickness or fraction thereof greater than one inch. In an embodiment, the heat treatment of the end sections yields a Brinell Hardness of from 270 to 301. In an embodiment, the vibrating flow tubes are quenched and tempered to yield a KSI yield strength of from 100 to 120.

In an embodiment, the HPVT densitometer is an all-welded construction. In an embodiment, the main non-temperature-sensitive components are welded together to form the PSA after the initial heat treatment described above and prior to the placement of internal components, including, but not limited to, the driver assembly, the pickup assembly and any sensors such as temperature sensors. As described herein, the pre-sensor assembly, PSA, comprises portals for the post-welding installation of these internal components.

In embodiments, a heat treatment is performed on the assembled PSA in order to allow stress relief of the various components at the welds. In an embodiment, the PSA is heat treated for stress relief at a temperature of between 900° F. and 1000° F. for 4 hours.

The PSA of the apparatus must be manufactured to an accuracy/tolerance such that the placement of internal components via the portals is adequate for proper functioning of the apparatus. In embodiments, the post-stress relief heat treatment placement of the temperature-sensitive internal components allows replacement of these components.

The internal components of the HPVT densitometer may be installed within the PSA by any method known to one of skill in the art. In embodiments, the driver/magnet coil pair and the pickup magnet/coil pair are mounted on brackets on each of the twin vibrating flow tubes, such that each tube has half of the magnet coil. In embodiments, the pairs are sandwiched together and screwed into place. In embodiments, the sensors are glued in place within the PSA. In embodiments, the sensors are set in place with an adhesive such as, for example, epoxy. In embodiments, the sensors are bolted in place.

The HPVT densitometer herein disclosed incorporates vibrating flow tubes in order to determine the density of the fluid flowing therethrough. This technique makes use of resonant tube vibration to measure fluid density. Using this technique, a fluid is passed through the twin vibrating flow tubes and vibrations are set up in the fluid-filled tubes. The resonant frequency of the tube(s) depends upon the inherent characteristics of the tube(s) and the fluid passing through the tube(s). For example, as the density of the fluid increases, the effective mass of the tube(s) also increases and the resonant frequency of the tube(s) decreases.

Discussing the operation of the apparatus of the present disclosure with reference now to FIG. 1, fluid flows into the HPVT densitometer from a connected pipeline on the inlet side of the densitometer. The fluid is directed through the vibrating flow tube(s), and exits the densitometer through the outlet side of the densitometer. The twin straight flow tubes 10 are excited by a signal from the controller 120 to the drive coil 40 and monitored to maintain resonant vibration. The natural vibration modes of the vibrating, fluid-filled system are defined in part by the combined mass of the flow tubes and the mass of the fluid flowing through the flow tubes. Pickup(s) are affixed to the flow tubes to measure the motion of the flow tube(s) and generate pickup response signals that are representative of the motion of the flow tube(s). Because the resonant vibration frequency varies with the weight of the fluid inside the tubes, the density of the fluid in the vibrating flow tubes 10 is related to and can readily be calculated from the measured resonant frequency.

As mentioned above, the HPVT densitometers of the present disclosure have a flow tube wall thickness three to four times that of the flow tube wall thickness of low pressure vibrating tube densitometers. As the thickness of the vibrating flow tube walls increases, the tubes do not flex as much in response to the signal from the controller. It thus takes more power for the tubes to remain vibrating. This leads to the need, in some embodiments, to incorporate an amplifier in order to amplify the signal from the controller to the driver magnet coil to increase the power level and achieve adequate vibration. In embodiments, the signal from the pickup must also be amplified by changing settings in the controller. For high pressure fluid density measurements, therefore, the driving and sensing of the motion of the flow tubes is more challenging than for the comparatively thin flow tubes of existing low pressure vibrating tube densitometers.

U.S. Pat. No. 3,444,723, also incorporated herein in its entirety, describes the operation and construction details of a low pressure vibrating tube densitometer which employs dual straight tubes.

The stresses on the vibrating flow tube(s) also affect the resonant frequency. These stresses are caused by various factors, including the hydrostatic pressure within or on the vibrating flow tubes and the temperature at various points within the densitometer. For example, for a simple structure, as the fluid pressure increases, the spring constant of the tube(s) increases, and the resonant frequency of the tube(s) increases. For more complex structures the resonant frequency of the tubes can decrease as pressure increases. Because these stresses affect the resonant frequency, it may be desirable to correct the density measurements for the temperature and pressure.

Because the outer shell of the HPVT densitometer of the present disclosure has a smaller ratio of the cross sectional area of the outer shell to that of the tubes, as discussed hereinabove, it may be desirable to measure the temperature of the outer shell and compensate the density reading accordingly in the case where the tubes are stretched or compressed axially. For example, if the outer shell is at a higher temperature, it expands, which increases the tension of the flow tubes, which may be envisioned as guitar strings. This increase in tension alters the frequency and thus the calculated density of the flowing fluid. Therefore, in embodiments, the temperature of the support structure is measured along with the temperature of the vibrating flow tubes. The controller reads the two (or more) temperatures, and adjusts the density accordingly, as is known to those of skill in the art.

As mentioned above, pressure compensation may be desirable to provide an accurate density value. An equation that may be used to correct the measured density is:

$$\rho_c = \rho_u + A*P \quad \text{(Equation 1)}$$

where $\rho_c$ is the corrected density, $\rho_u$ is the uncorrected density, A is a constant, and P is the fluid pressure. The constant A can be approximated from structural analysis calculations and refined during calibration of the HPVT densitometer. In an embodiment, pressure, P, and uncorrected density, $\rho_u$, signals are passed to a data acquisition or control system for calculation of the corrected density, $\rho_c$. Pressure compensation is discussed in U.S. Pat. Nos. 6,732,570 and 6,868,740 and WO 96/08967, each of which is incorporated by reference herein in its entirety.

As mentioned previously, the HPVT densitometer of the present disclosure may be suitable for the measurement of the density of various high pressure fluids, for example the HPVT densitometer may be used to determine the density of fracturing fluids and cements in the oil field.

During fracturing operations, a "frac" slurry is formed and pumped from a blender to a high pressure pumping unit, which increases the pressure of the slurry up to about 15,000 psi. A "treating" line carries the high pressure "frac" slurry to the wellhead. In an embodiment, the connected pipeline to which the HPVT densitometer is attached is a treating line between the high pressure pump and the wellhead.

During cementing operations, components of a cement slurry are mixed together, and the cement slurry is conveyed to a high pressure pumping unit, where the pressure of the slurry is increased up to about 15,000 psi. One or more high pressure discharge lines carry the cement slurry to the wellhead. In an embodiment, the connected pipeline to which the HPVT densitometer is attached is at least one high pressure discharge line located downstream of a high pressure pump.

In some embodiments, for example, the U-tube sensor body configuration of FIG. 2, a slipstream of fluid may be diverted to the densitometer wherein the density of the fluid in the slipstream is determined. In various embodiments the "treating" line, the high pressure discharge line, or other connected pipeline would provide appropriate connection to the HPVT densitometer. For example, in the embodiment of FIG. 3, the connected pipeline would serve to split the stream prior to entering the densitometer.

The HPVT densitometer may be connected to the connected pipeline by any method known to one of skill in the art. As discussed hereinabove, the HPVT densitometer may be attached to the connected pipeline via standard hammer unions. In embodiments, the HPVT densitometer has the same flow area as a standard 15,000 psi discharge joint of the same nominal diameter. In embodiments, the HPVT densitometer has been ruggedized to withstand the force applied when attaching the densitometer to a connected pipeline. For example, the driver of the HPVT densitometer may be resistant to the shock experienced upon hammering of union joints.

While preferred embodiments of the apparatus and method for making the apparatus have been shown and described, modifications thereof can be made by one skilled in the art without departing from the spirit and teachings of the present disclosure. The embodiments described herein are exemplary only, and are not intended to be limiting. For example, while the fluids referred to in this disclosure are commonly encountered in the oilfield, the HPVT densitometer of the present disclosure is suitable for the measurement of the density of other fluids as well. Many variations and modifications of the apparatus and methods disclosed herein are possible and are within the scope of this disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, etc.). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, etc.

Accordingly, the scope of protection is not limited by the description set out above but is only limited by the claims which follow, that scope including all equivalents of the subject matter of the claims. Each and every claim is incorporated into the specification as an embodiment of the present disclosure. Thus, the claims are a further description and are an addition to the preferred embodiments of the present disclosure. The discussion of a reference herein is not an admission that it is prior art to the present disclosure, especially any reference that may have a publication date after the priority date of this application. The disclosures of all patents, patent applications, and publications cited herein are hereby incorporated by reference, to the extent that they provide exemplary, procedural or other details supplementary to those set forth herein.

What is claimed is:

1. A vibrating tube densitometer system for determining the density of a high pressure fluid in a pipeline, the system comprising a densitometer in communication with a controller, the densitometer comprising:
    twin straight flow tubes spaced parallel apart within an outer shell comprising one or more resealable portals for the placement, replacement, and operation of internal components, said internal components comprising:
        a driver positioned adjacent the twin flow tubes for initiating and maintaining resonant vibration of the twin flow tubes;
        at least one pickup positioned adjacent the twin flow tubes for sensing the motion of at least one twin flow tube and transmitting a signal indicative of the response of the vibration of the at least one flow tube; and
        at least one temperature or pressure sensor,
    wherein the controller is in signal communication with the pickup, the driver, and the at least one temperature or pressure sensor and calculating the density of a fluid having a pressure of greater than 1500 psi.

2. The densitometer system of claim 1, wherein the temperature sensor comprises a thermocouple, a resistive temperature device, a thermistor, or combinations thereof.

3. The densitometer system of claim 1, wherein the driver further comprises a driver magnet attached to one twin flow tube and a coil attached opposite the driver magnet on the other twin flow tube.

4. The densitometer system of claim 1, wherein the pickup comprises a piezo-based accelerometer, a magnet-coil velocity sensor, or combos thereof.

5. The densitometer system of claim 1, wherein the densitometer further comprises a U-shaped end section connecting an outlet end of one flow tube to an inlet end of the other flow tube.

6. The densitometer system of claim 5, wherein the first and second Y-shaped end sections each further comprise a hammerless union.

7. The densitometer system of claim 1, wherein the densitometer further comprises a first Y-shaped end section connecting inlet ends of the flow tubes and a second Y-shaped end section connecting outlet ends of the flow tubes.

8. The densitometer system of claim 1, wherein the controller is coupled to a temperature sensor and a pressure sensor, wherein the controller provides a density measurement corrected for sensed temperature and pressure.

9. The densitometer system of claim 1, wherein the flow tubes and the outer shell are heat treated.

10. A method of determining the density of a wellbore servicing fluid comprising:
    pumping the fluid at a pressure of greater than or equal to 1500 psi to a resonant vibrating tube densitometer comprising:
    twin vibrating flow tubes; and
    one or more resealable portals for the installation, replacement, and operation of internal components,
    wherein resonant vibrations of at least one of the fluid-filled vibrating tubes are used to determine the density of the high pressure fluid.

11. The method of claim 10 further comprising correcting the density by compensating for the effects of fluid pressure and the temperature of at least one position within or on the densitometer.

12. The method of claim 10 further comprising closing the portals upon installation of the internal components.

13. The method of claim 12 further comprising re-opening one or more of the portals to add or remove an internal component.

* * * * *